United States Patent [19]

Koontz et al.

[11] Patent Number: 5,179,025

[45] Date of Patent: Jan. 12, 1993

[54] ATMOSPHERIC PRESSURE FLOW REACTOR: GAS PHASE CHEMICAL KINETICS UNDER TROPOSPHERIC CONDITIONS WITHOUT WALL EFFECTS

[75] Inventors: Steven L. Koontz, League City, Tex.; Dennis D. Davis, Las Cruces, N. Mex.

[73] Assignee: The United States of America as represented by the United States National Aeronautics and Space Administration, Washington, D.C.

[21] Appl. No.: 737,756

[22] Filed: Jul. 30, 1991

Related U.S. Application Data

[62] Division of Ser. No. 279,170, Dec. 2, 1988, Pat. No. 5,077,015.

[51] Int. Cl.$^5$ .................... G01N 35/08; G01N 31/00; G01N 7/00; G05D 7/00
[52] U.S. Cl. ........................................ 436/52; 436/9; 436/117; 422/83; 422/93; 422/110
[58] Field of Search ............... 436/9, 52, 117; 422/83, 422/93, 176, 110; 137/889, 896; 73/23.2, 31.07

[56] References Cited

U.S. PATENT DOCUMENTS

| | | | |
|---|---|---|---|
| 3,482,431 | 12/1969 | Mochizuki | 73/23.2 |
| 3,649,829 | 3/1972 | Randolph | 73/23.2 |
| 3,713,773 | 1/1973 | Fontijin et al. | 436/117 |
| 4,042,328 | 8/1977 | Seymour | 436/52 |
| 4,311,669 | 1/1982 | Spangler | 422/98 |
| 4,941,345 | 7/1990 | Altemark et al. | 73/23.2 |
| 4,960,711 | 10/1990 | Aoki et al. | 436/124 |

Primary Examiner—Robert J. Warden
Assistant Examiner—Christopher Y. Kim
Attorney, Agent, or Firm—Edward K. Fein; Guy M. Miller; Russell E. Schlorff

[57] ABSTRACT

A flow reactor for simulating the interaction in the troposphere is set forth. A first reactant mixed with a carrier gas is delivered from a pump and flows through a duct having louvers therein. The louvers straighten out the flow, reduce turbulence and provide laminar flow discharge from the duct. A second reactant delivered from a source through a pump is input into the flowing stream, the second reactant being diffused through a plurality of small diffusion tubes to avoid disturbing the laminar flow. The commingled first and second reactants in the carrier gas are then directed along an elongate duct where the walls are spaced away from the flow of reactants to avoid wall interference, disturbance or turbulence arising from the walls. A probe connected with a measuring device can be inserted through various sampling ports in the second duct to complete measurements of the first and second reactants and the product of their reaction at selected XYZ locations relative to the flowing system.

5 Claims, 1 Drawing Sheet

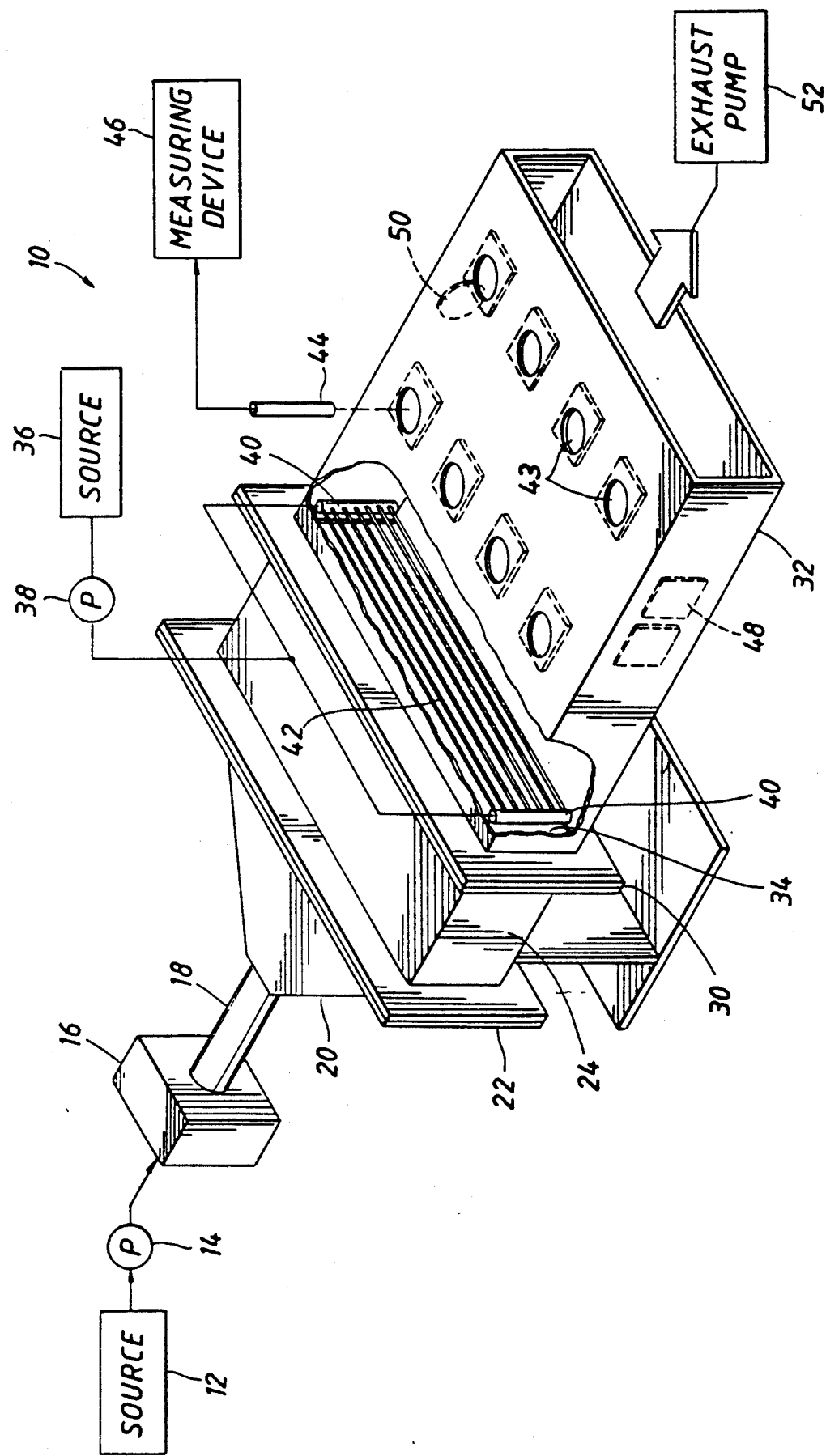

ATMOSPHERIC PRESSURE FLOW REACTOR: GAS PHASE CHEMICAL KINETICS UNDER TROPOSPHERIC CONDITIONS WITHOUT WALL EFFECTS

ORIGIN OF THE INVENTION

This is a division of application Ser. No. 279,170 filed Dec. 2, 1988, now U.S. Pat. No. 5,077,015.

The invention described herein was made by employee(s) of the United States Government and may be manufactured and used by or for the Government of the United States of America for governmental purposes without the payment of any royalties thereon or therefor. (Stat. 435; 42 U.S.C. 2457).

TECHNICAL FIELD

The present disclosure is directed to a device method in which atmospheric gas reaction and diffusion studies can be conducted. Substantial scientific inquiry has been directed to the interaction of first and second gas reactants as will typically occur in atmospheric circumstances at all elevations ranging from the immediate surrounding atmosphere to outerspace. For instance, wide spread public speculation on the "green house" impact can be resolved only by serious studies of the interaction of atmospheric gases. As an example, allegations are made that various fluorocarbons utilized in aerosol canisters and the like have partially depleted the ozone layer which is essential to protection of the earth from certain effects of the sun's radiation. Any study of this phenomenon inquires into the diffused interaction (chemical kinetics) of first and second reactants in a simulated atmosphere. The present apparatus is a system whereby rates of reaction between first and second reactants can be measured to thereby determine the impact at various heights of the earth's atmosphere from the immediate near earth location to higher elevations where the atmospheric pressure is reduced.

BACKGROUND ART

Significant references which have a bearing on the present system and apparatus include U.S. Pat. No. 3,713,773 which discloses an apparatus for analyzing gas samples. A first gaseous reactant is fed into a flow stream made of a second gas reactant and the gas product is analyzed downstream after mixing. There is no disclosure of flow straightening mechanisms and the feed of the first reactant is altogether different.

In U.S. Pat. No. 4,048,586, a chemical laser has a feed tube 15 with small holes at 16a, 16b, etc. and is arranged to introduce gas into a gaseous flow stream at FIG. 1 thereof. No effort is made in the described apparatus to accomplish laminar flow conditions within the reactor.

U.S. Pat. No. 4,360,923 discloses an apparatus which reacts first and second gases in a chemical laser to obtain a uniform reaction rate. FIGS. 3 and 4 thereof show a panel 24 made up of a number of mixer tubes with a view of obtaining feed for the mixer tubes 20. Injection occurs thereafter.

In U.S. Pat. No. 4,230,996, a chemical laser incorporates a plurality of tubular manifolds to feed gas uniformly across a given area. Extreme high operating temperatures are involved in this structure which supports a nozzle array.

ADVANTAGES OF THE PRESENT APPARATUS

This apparatus and the method of use thereof relate primarily to conducting diffusion reaction experiments at a given atmospheric pressure wherein one gas reactant is mixed into or otherwise injected into a flowing carrier gas with reactant. Diffused reactant interaction is thus determined, and as a consequence thereof, the reactant chemical kinetics can then be determined by subsequent measuring instruments inserted downstream which provide dynamic reactant concentration measurements.

One of the problems that must be avoided is the interaction of surrounding walls with the flowing gas stream and reactants which are mixed together in a controlled fashion to achieve the requisite conditions whereby the desired process can be measured. The present apparatus thus avoids significant limitations of prior art devices. The present apparatus is able to achieve desirable experimental conditions suitably mimicking conditions even in the troposphere. This in part is achieved by reducing, even eliminating, substantial interaction with the surrounding walls of the structure. In other words, the two reactants are still mixed by molecular diffusion with a modest level, almost negligible, small scale turbulence occurring at the point at which the second reactant is injected. The present apparatus and method of use thus provide a structure and method which assure that the carrier flow and reactant is flowing in a substantially laminar fashion with minimal engagement with the surrounding walls of the structure. The second reactant is introduced downstream and is thus involved only in laminar flow, and moreover, the second reactant is introduced in a fashion to hold to a minimum microscopic disturbances such as eddy currents in the locale of the injection. The second reactant is thus injected through porous tubes which permit resultant second reactant diffusion into the surrounding atmosphere. The surrounding atmosphere is a uniform, constant, laminar flow of a carrier gas at a single velocity, and point measurements are made downstream therefrom at defined XYZ locations. The data thus can be provided in an organized form to show concentration of the product of reaction at an XYZ locations substantially free of impact from surface reaction on the surrounding structure.

BRIEF DESCRIPTION OF THE DRAWINGS

So that the manner in which the above recited features, advantages and objects of the present invention are attained and can be understood in detail, more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

The single view of the present disclosure is an isometric showing a first reactant flow system utilizing a suitable carrier source and pump for a first reactant and including a means for obtaining laminar fluid flow, and further including a second reactant source and pump to introduce a second reactant through a second set of tubes for infiltration into the flowing first reactant wherein the carrier flow is conducted along a lengthwise duct with substantial spacing to avoid interaction with the walls.

DETAILED DESCRIPTION OF THE PREFERRED AND ILLUSTRATED EMBODIMENT

Attention is first directed to the only drawing incorporated with this disclosure which shows in isometric view a flow reactor identified generally by the numeral 10. It includes a chamber or housing which completely surrounds the reactants so that the pressure at which the reaction occurs can be controlled, typically in the range of zero to 1.0 ATM to provide experimental conditions representative of the troposphere. The internal pressure can be adjusted to lower or higher pressures within the specified range as will be explained. The flow reactor 10 of the present apparatus cooperates with a first reactant. This is the first reactant (with a carrier gas) in the two gas system to be described. It is delivered from a source 12 through a pump 14 and is introduced through a control valve and control system 16. The first reactant is normally mixed with a carrier gas (e.g., dry nitrogen) in some ratio and is delivered at a controlled flow rate resulting in a desired velocity. In turn, it flows through an outlet conduit 18 into a fan shaped diffuser duct 20. That terminates at an upstanding set of flanges which are identified at 22, and they support by clamping therebetween a flow straightening screen (not shown). In turn, the flanges support a duct 24 which is rectangular in cross-section and which has a specified length, and may contain flow straightening louvers.

The duct terminates at a set of flanges 30 which enable attachment of a downstream reactor chamber 32. It is also constructed in the fashion of a duct. It has approximately equal width and height compared to the duct 24. The duct 24 is open at one wall to introduce laminar flow out of the duct 24 into the reactor 32. There is a window 34 which communicates from the duct 24 to the duct 32. The window is equal in dimensions to both of the two ducts. The two sets of flanges hold perforate screens in position. They are solid inserts, clamped in place, and are perforated with a great number of small holes to enable fluid flow to be moderated by the fluids to flow evenly into the aligned ducts.

The numeral 36 identifies a source of a second reactant which is delivered through a pump 38. This pump delivers the second reactant into a header 40 (preferably one at each end of the window) which connects with a plurality of quite small, partly porous flow lines 42. The lines 42 are porous in the central portions and are nonporous at the end portions. This enables reactant injection to be limited to a controlled and defined rectangular region. The porous part of the flow lines 42 extend across a specified region of the window 34. Relative dimensions may assist in providing an understanding of injection. The active reagent injection zone has a width and height which is less than the width and height of the reactor 32, thereby assuring that the first reactant does not contact the walls of the reactor 32. The lines 42 are preferably small in diameter, formed of porous materials, and introduce the second reactant through the tube walls. The second reactant introduction procedure will be described in detail hereinafter. The precise arrangement of the lines 42 is preferably a plurality of parallel, horizontal small tubular members, the members being sufficiently small that the turbulence created in the first reactant flowing therepast is nil. This flow is carried downstream from the point of introduction where the reactants begin to commingle and initiate the reaction under investigation in three dimensional space free of wall impact as will be described.

The reactor 32 is a confining wall. It is a wall having a number of closed ports 43 formed at various locations around the top. A probe 44 can be inserted through the various ports 43 to make measurements. The probe can make velocity measurements of the gas stream flowing along the reactor 32. The probe 44 optionally may obtain a small sample and delivers it to a measuring device 46 which provides an output signal indicative of the concentration of the first and second reactants or their products. The preferred reactant measuring system is a long path spectroscopic cell (a so-called White cell). This is installed to direct light across the reactor 32 along a multiple segment folded pathway using side wall mirrors 48 and light source 50. They are mounted to reflect back and forth through the reacted materials so that reaction conversion can be measured. In other words, the first and second reactants diffuse among one another, diffusion literally occurring at the molecular level, and the reactants interact to form a product. The measuring device is operated to measure the concentration of the reactants and or products. The reaction within the chamber 32 is a function of concentrations of the first and second reactants. Moreover it is also a function of the velocity of the reactant flow through the duct 32. For purposes of precise measurement, an XYZ coordinate system is defined within the reactor chamber 32 so that concentrations of the two reactants can be measured at various locations, and also so that the product concentration can be indicated at various locations through the chamber 32. Accordingly, the XYZ coordinate system permits a generalized expression of product concentration. The chamber 32 terminates at an exhaust pump 52 which pulls the reactants and carrier gas out of the chamber at a controlled pressure. The wall is a solid member with closed parts and is therefore able to sustain pressures above or below ambient pressure.

The XYZ coordinate system can be defined at any point serving as the origin. Preferably, the origin is located so that it coincides with the second reactant injector lines 42. More specifically, the origin of the coordinate system can arbitrarily be fixed at the mid point of the injection lines 42 so that symmetry is accomplished on both sides of the origin. By observation of data taken at various points through the chamber, turbulence associated with interaction of the walls which confine the flow is substantially reduced and does not significantly impact such data or measurements. Consider one example, namely the reaction of hydrazine with ozone. Hydrazine interaction with ozone is an atmospheric reaction resulting from escaping fuel. Typical assumptions for an atmospheric test assume ozone to be present at a concentration of about $3.0 \times 10^{-8}$ mole/cc in an inert carrier gas flowing at 10 cm/second. The reaction rate constant for hydrazine and ozone is $10^{-16}$ cm$^2$/molecule/sec. The diffusion coefficient for hydrazine is 0.39 cm$^2$/sec. Moreover, the pressure was 1 ATM, and temperature was 300° K. Measurements made at a variety of locations in the chamber 32 indicate substantially no interaction of the walls with the diffusion process of the reactants. While reactant concentrations are not uniform and hence the reaction obtained thereby is not homogeneous, such measurements that are obtained indicate a substantial absence of wall reaction interference. In the example mentioned, the hydrazine reaction kinetics in the troposphere can thus be evaluated utilizing the illustrated flow reactor.

As will be understood, alternate first and second reactants can be used, and it is also possible to mix reactants so that either reactant is a single compound or can be a mixture as would be considered in evaluating the effect of flue gases. This finds use in the evaluation of $SO_x$ and $NO_x$ typically discharged from large industrial plants and diffused into the atmosphere. Moreover, the present system enables such measurements to be accomplished and test data gathered in a context where test instrumentation does not create turbulence, thereby disrupting the laminar flow achieved in the system as illustrated so that proper measurements can be obtained.

While the foregoing is directed to the preferred embodiment, the scope thereof is determined by the claims which follow.

We claim:

1. A method for determining the interaction of first and second reactants in simulation of atmospheric interactions, the method comprising:
   (a) providing a carrier gas, a first reactant, and a second reactant;
   (b) mixing the first reactant with the carrier gas containing the first reactant and delivering the carrier gas for flow of the carrier gas containing the first reactant through a duct;
   (c) directing the flow through said duct to form laminar flow of carrier gas containing the first reactant;
   (d) directing the laminar flow of carrier gas containing the first reactant including the first reactant into a second duct in fluid communication with said first duct;
   (e) introducing the second reactant into the laminar flow of carrier gas containing the first reactant into the second duct wherein the introduction is accomplished through a diffusion means relatively centered with respect to the second duct that the diffusion is accomplished substantially without disturbing the laminar flow of the first reactant, and further wherein the second duct is defined by walls which are spaced sufficiently from the introduction of the second reactants that laminar flow carries the first and second reactants along with the laminar flow and permits molecular scale diffusion and interaction of the first and second reactants while moving in laminar flow; and
   (f) determining the interaction of the first and second reactants in the second duct.

2. The method of claim 1 including the step of introducing a sample probe into the laminar flow of carrier gas containing the first and second reactants for measuring concentrations of reactants and products of reaction.

3. The method of claim 1 including the step of directing the laminar flow of carrier gas containing the first and second reactants after diffusion of the second reactant for a specified length with said second duct.

4. The method of claim 3 wherein the entire method is conducted in an atmosphere having a regulated pressure.

5. The method of claim 4 including the step of introducing a sample probe into the laminar flow of carrier gas containing the first and second reactants for measuring concentrations of reactants and products of reaction.

* * * * *